US006849401B1

(12) United States Patent (10) Patent No.: US 6,849,401 B1
Andersson et al. (45) Date of Patent: Feb. 1, 2005

(54) METHODS FOR DETERMINING COAT COLOR GENOTYPES IN PIGS

(75) Inventors: Leif Andersson, Uppsala (SE); Stefan Marklund, Uppsala (SE); James Kijas, Ithaca, NY (US); Maria Moller, Uppsala (SE); Richard Wales, Cambridge (GB)

(73) Assignee: Melica HB (SE)

( * ) Notice: Subject to any disclaimer, the term of this patent is extended or adjusted under 35 U.S.C. 154(b) by 0 days.

(21) Appl. No.: 09/550,605

(22) Filed: Apr. 17, 2000

Related U.S. Application Data

(63) Continuation-in-part of application No. PCT/GB98/03081, filed on Oct. 13, 1998.

(30) Foreign Application Priority Data

Oct. 17, 1997 (GB) .............................................. 9722027

(51) Int. Cl.[7] .......................... C12Q 1/68; G01N 33/53; C12P 19/34; C07H 21/04
(52) U.S. Cl. ............................. 435/6; 435/71; 435/91.2; 536/23.1; 536/24.3
(58) Field of Search .......................... 435/6, 7.1, 91.2, 435/91.1; 536/23.1, 24.3

(56) References Cited

U.S. PATENT DOCUMENTS

| | | | |
|---|---|---|---|
| 5,545,533 A | 8/1996 | Bartke et al. | |
| 6,183,955 B1 | 2/2001 | Andersson et al. | |
| 6,218,119 B1 | * 4/2001 | Kuiper et al. | ................... 435/6 |

FOREIGN PATENT DOCUMENTS

| | | |
|---|---|---|
| WO | WO 92/18651 A1 | 10/1992 |
| WO | WO 93/10136 A1 | 5/1993 |
| WO | WO 96/41892 A1 | 12/1996 |
| WO | WO 9705278 | 2/1997 ................... 435/6 |
| WO | WO 99/20795 A1 | 4/1999 |

OTHER PUBLICATIONS

Ahern, Holly from :The Scientist, vol. 9, 1995. pp. 1–5.*
New England Biolabs (1996 catalog, p. 42).*
Ohler et al., PCR Methods and Applications, vol. 3, pp 115–119, 1993.*
M. Johansson Moller, et al., "Pigs with the Dominant White Coat Color Phenotype Carry a Duplication of the KIT Gene Encoding the Mast/Stem Cell Growth Factor Receptor," *Mammalian Genome*, vol. 7, pp 822–830 (1996).
Stefan Marklund, et al., "Molecular Basis for the Dominant White Phenotype in the Domestic Pig," *Genome Research*, vol. 8, pp 826–833 (1998).
Andersson et al., "Genetic Mapping of Quantitative Trait Loci for Growth and Fatness in Pigs," Science, vol. 263, Mar. 25, 1994, pp. 1771–1774.

Bernstein et al., "The mouse WIc–kit locus," Molecular Control of Haemopoiesis, Ciba Foundation Symposium 148, Published by John Wiley & Sons, 1990, pp. 158–172.
Besmer et al., "A new acute transforming feline retrovirus and relationship of its oncogene v–kit with the protein kinase gene family," Nature, vol. 320, Articles, Apr. 3, 1986, pp. 415–421.
Chabot et al., "The proto–oncogene c–kit encoding a transmembrane tyrosine kinase receptor maps to the mouse W locus," Nature, vol. 335, Letters Tonature, Sep. 1988, pp. 88–89.
De Sepulveda et al., Instability at the W/c–kit locus in mice : analysis of melanocyte cell lines derived from reversion spots, Oncogene, vol. 9, 1994, pp. 2655–2661.
Ezashi et al., "The gene for the Beta subunit of porcine LH: clusters of GC boxes and CACCC elements," Journal of Molecular Endocrinology, vol. 5, 1990, pp. 137–146.
Fleischman et al., "Deletion of the c–kit protooncogene in the human developmental defect piebald trait," Proc. Natl. Acad. Sci., vol. 88, Dec. 1991, pp. 10885–10889.
Giebel et al., "Organization and nucleotide sequence of the human KIT (mast/stem cell growth factor receptor) proto–oncogene," Oncogene, vol. 7, 1992, pp. 2207–2217.
Geissler et al., "The dominant–white spotting (W) locus of the mouse encode the c–kit Proto–Oncogene," Cell, vol. 55, Oct. 1998, pp. 185–192.
Gokkel et al., "Structural organization of the murine c–kit proto–oncogene," Oncogene, vol. 7, 1992, pp. 1423–1429.
Johansson et al., "The Gene for Dominant White Color in the Pig is Closely Linked to ALB and PDGFRA on Chromosome 8," Genomics 14, 1992, pp. 965–969.
Kato et al., "The gene for the common alpha subunit of porcine pituitary glycoprotein hormone," Journal of Molecular Endocrinology, vol. 7, 1991, pp. 27–34.
Nocka et al., Molecular bases of dominant negative and loss of function mutations at the murine c–kit/white spotting locus: W37, Wv, W41 and W, The EMBO Journal, vol. 9, No. 6, 1990, pp. 1805–1813.
Rohrer et al., "A Microsatellite Linkage Map of the Porcine Genome," Genetics, vol. 136, Jan. 1994, pp. 231–245.
Coppieters et al., "Characterization of Porcine Polymorphic microsatellite loci," Animal Genetics, 24, 1993, pp. 163–170.
Ellegren et al., "Assignment of 20 Microsatellite Markers to the Porcine Linkage Map," Genomics, 16, 1993, pp. 431–439.
PCT International Preliminary Examination Report for PCT/GB98/03081.
PCT Written Opinion for PCT/GB98/03081.
PCT International Search Report for PCT/GB98/03081.

* cited by examiner

*Primary Examiner*—Jehanne S. Sitton
(74) *Attorney, Agent, or Firm*—Hunton & Williams LLP

(57) ABSTRACT

Methods for determining coat color genotypes in pigs are provided. In particular, these methods are based on determining whether a mutation is/is not present at one or more exon/intron splice sites of the KIT gene. Kits for carrying out such methods are also described.

15 Claims, 8 Drawing Sheets

Figure 1:
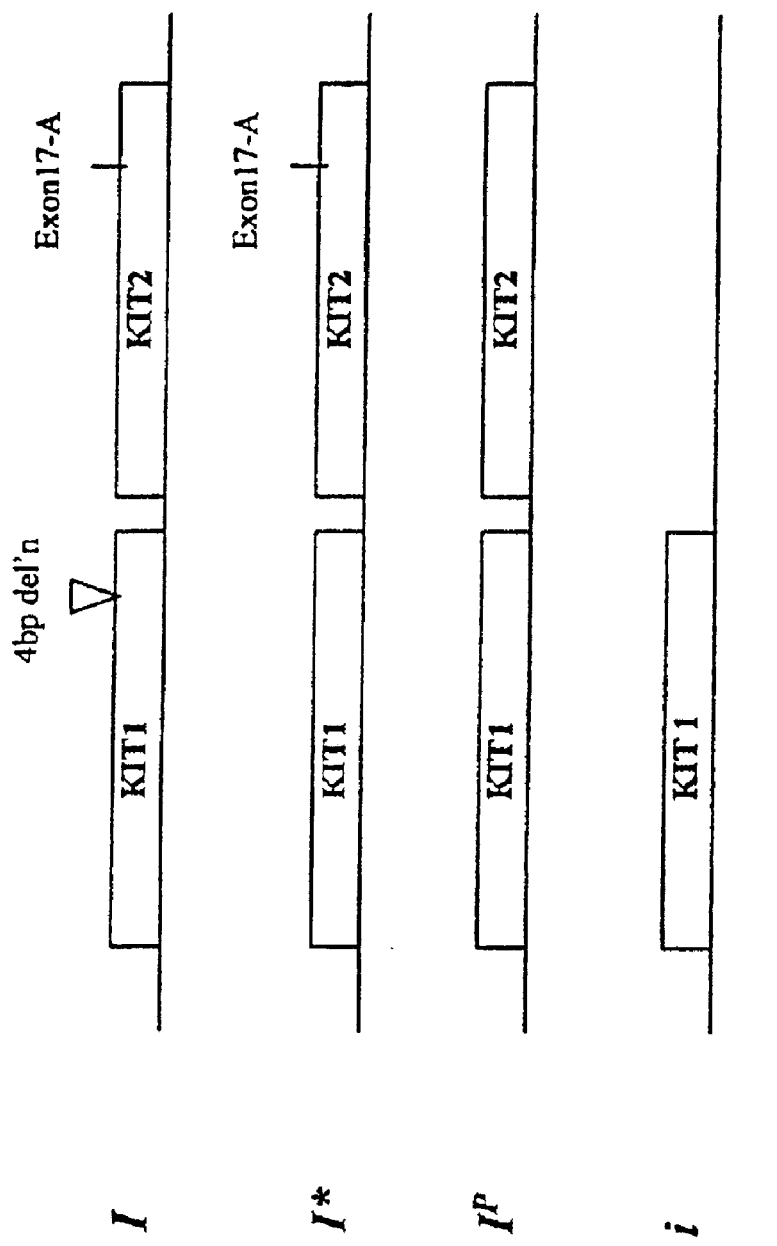

Sequence Alignment Across the Exon /Intron Border of KIT Exon 17

```
Allele  Gene Copy           Sequence
                    Exon 17   Intron 17
                                      ↓
  I      KIT1   AAT TAC GTG GTC AAA GGA AAC|GTG AGT ACC CAC GCT CTC CTG ACA GTC
         KIT2   ... ... ... ... ... ... ...|A.. ... ... ... ... ... ... ... ...

I^F    KIT1   ... ... ... ... ... ... ...|G... ... ... ... ... ... ... ... ...
         KIT1   ... ... ... ... ... ... ...|G.. ... ... ... ... ... ... ... ...

i      KIT1   ... ... ... ... ... ... ...|G.. ... ... ... ... ... ... ... ...
```

FIG.3

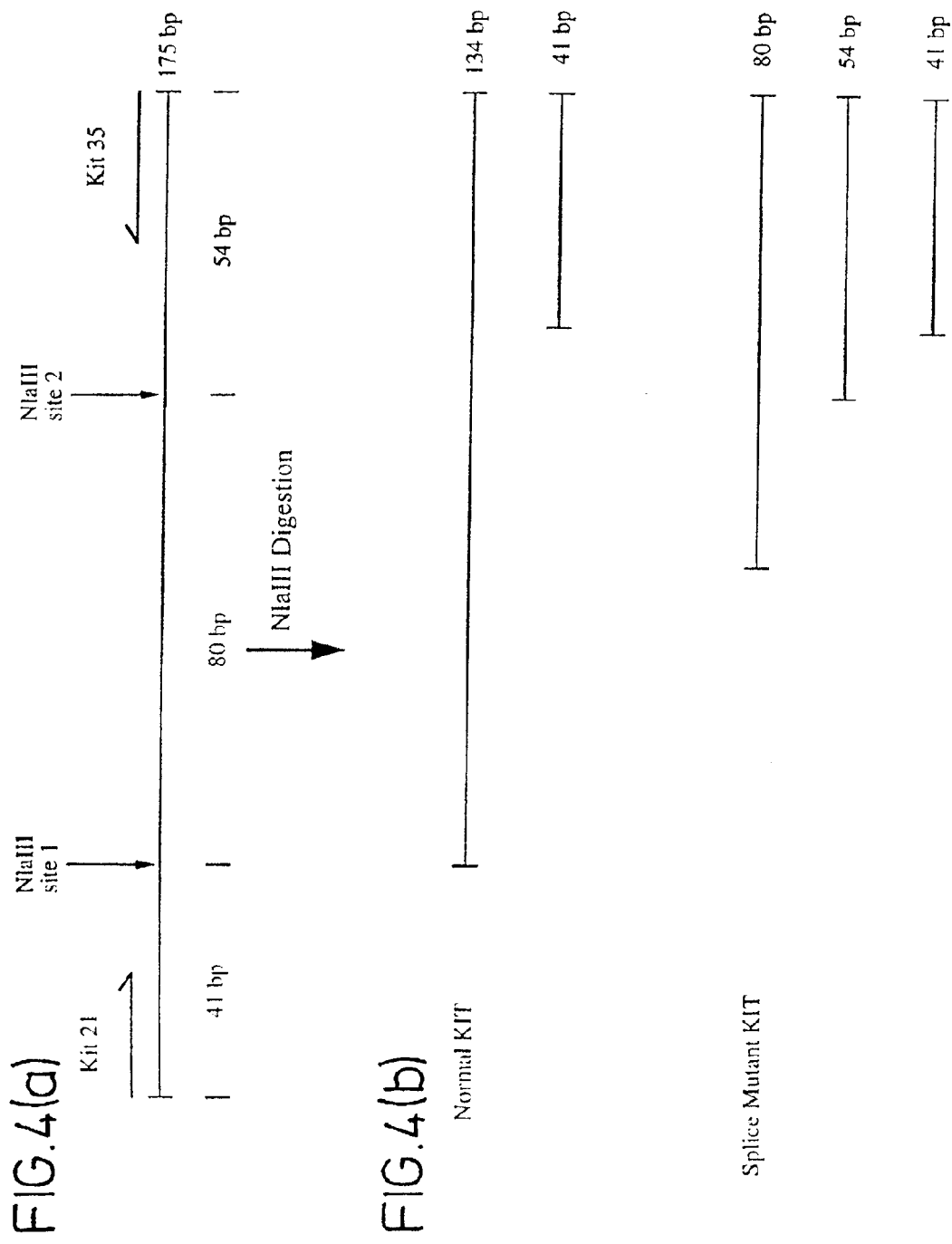

SEQUENCE LISTING

<160> NUMBER OF SEQ ID NOS: 11

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
gtattcacag agacttggcg gc                                    22

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
aaacctgcaa ggaaaatcct tcacgg                                26

<210> SEQ ID NO 3
<211> LENGTH: 25
<212> TYPE: DNA

```
<213> ORGANISM: Artificial Sequence
<220> FEATURE:
<223> OTHER INFORMATION: Primer

<400> SEQUENCE: 3
tcrtacatag aaagagaygt gactc                                  25

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
agccttcctt gatcatcttg tag                                    23

<210> SEQ ID NO 5
<211> LENGTH: 26
<212> TYPE: DNA
<213> ORGANISM: Artificial Sequence
<220> FEATURE:
<223> OTHER INFORMATION: Primer

<400> SEQUENCE: 5
aaacctgcaa ggaaaatcct tcacgg                                 26

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
ctccttactc atggtcgaat caca                                   24

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
cggctaaaat gcatggtatg g                                      21

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
tcaaaggaaa catgagtacc cacgctc                                27

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
tcaaaggaaa cgtgagtacc cacgc                                  25
```

```
<210> SEQ ID NO 10
<211> LENGTH: 48
<212> TYPE: DNA
<213> ORGANISM: Sus scrofa

<400> SEQUENCE: 10
aattacgtgg tcaaaggaaa cgtgagtacc cacgctctcc tgacagtc          48

<210> SEQ ID NO 11
<211> LENGTH: 48
<212> TYPE: DNA
<213> ORGANISM: Sus scrofa

<400> SEQUENCE: 11
aattacgtgg tcaaaggaaa catgagtacc cacgctctcc tgacagtc          48
```

METHODS FOR DETERMINING COAT COLOR GENOTYPES IN PIGS

This application is a continuation-in-part of PCT/GB98/03081, filed Oct. 13, 1998.

The present invention relates to methods for determining coat colour genotype in pigs. In particular, it relates to methods of distinguishing between the alleles I, $I^P$, I* and i of the KIT gene.

Coat colour is important to the pig breeding industry for a number of reasons. Firstly in a number of markets there is a preference for white skinned meat. This is due to the fact that pork is often marketed with the skin still attached, and skins from coloured pigs, even if dehaired, can still exhibit coloured hair roots, which can lead to negative perception by the consumer, since the surface of the meat may appear to be spotted by mould. It is therefore necessary in these markets to remove the skin from such carcasses, entailing additional cost For example, in the US, coloured carcasses are associated with approximately 1% of skin defects requiring dehairing and skinning to remove pigment. As a result of this, coloured pig carcasses are generally discounted. Secondly gross variation in the appearance of pigs claimed to be genetically consistent for other traits can lead to questions about the consistency and quality of the animals in the mind of pig-producing customers. Breeders would also like to be able to ensure consistency in breeding populations. Thus breeders may wish to ensure that progeny produced by breeding crosses were always white. Alternatively a breeder producing a coloured breed may wish to ensure that the correct coat colour characteristics were maintained even during the introgression of genes from white lines.

White coat colour in pigs is controlled by the dominant white locus designated I (for inhibition of coat colour). Structural alterations in the porcine KIT gene have recently been correlated with various alleles of I and are probably responsible for the differences in coat colour pattern found or are closely linked to the mutations that are found (Johansson Moller et al. 1996 Mammalian Genome 7, 822–830). Four structural versions of the porcine KIT gene have been identified to date and designated I, $I^P$, I* and i (see FIG. 1 and table 1). The version found in filly coloured animals including wild boar and which is therefore generally accepted as the wild type allele is i. The other versions of the gene known all involve duplication of at least part of the porcine KIT gene. $I^P$ is a partially dominant allele and causes in the heterozygous state ($I^P$/i) a phenotype "patch" characterised by patches of white and coloured coat. I and I* are both fully dominant and cause a white phenotype both in the heterozygous and homozygous state. The only difference between I and I* is that there is a 4 bp deletion in intron 18 in one of the two KIT gene copies associated with the I allele. This sequence polymorphism is not expected to have any functional effect.

The phenotypes of a number of gene combinations are listed below with the I allele being dominant over $I^P$ and i, and $I^P$ being dominant over i (Johansson et al. 1992 Genomics 14, 965–969)

| Genotype | Colour |
|---|---|
| I/I | White |
| I/$I^P$ | White |
| I/i | White |
| $I^P$/i | Patched |
| i/i | Coloured |
| I*/i | White |

Previously Moller Johansson et al. (1996 Mammalian Genome 7, 822–830) revealed that KIT occurs as a single copy gene in coloured (i/i) animals but is duplicated in the I, I* and $I^P$ allele. This duplication allowed the differentiation of I, I* and $I^P$ from i through examination of the gene copy number of KIT and to use linked polymorphisms in or in the near vicinity of the KIT gene to distinguish different alleles at the I locus. This approach is the subject of International patent WO97/05278.

A problem remaining from this method however is that it does not distinguish between I* and $I^P$. The result of this is that if one wishes to use the screen to remove heterozygous carrier animals of genotype I/$I^P$ from a white pig line one also excludes I/I* animals unnecessarily. The removal of animals, potentially very valuable if at the top of a breeding pyramid, unnecessarily can lead to a reduction in the rate of improvement of other traits within that particular group of animals. Other consequences include a general loss of genetic diversity land a loss of alleles at the locus in question that may have as yet undetected value. It is essential that one only excludes alleles where absolutely necessary.

Further sequence analysis of genomic DNA revealed a mutation at the first nucleotide in intron 17 of KIT2 leading to a defect in the splicing of RNA transcribed from this particular copy of the KIT gene. In experiments involving several pig breeds, this mutation showed a complete concordance with the presence of the I and I* alleles but was not found in the i and $I^P$ alleles The majority of eukaryotic genes are composed of both coding (exon) and intervening noncoding (intron) regions. The latter of these sequences are removed from large pre-mRNA by a highly accurate cleavage and ligation reaction known as splicing. The result is a mature mRNA transcript, devoid of intron sequences, which is transported to the cytoplasm for translation. The splicing of eukaryotic genes is most likely a two step procedure. First the pre-mRNA is cleaved at the 5' (donor) splice site followed by cleavage at the 3' (acceptor) splice site. The second step involves rejoining of the spliced exons to result in exclusion of the intervening intron. Splicing is therefore critically dependant on the accuracy of the cleavage and ligation reactions. This accuracy appears to be dependant on the almost completely invariant GT and AG dinucleotides present at the 5' and 3' exon/intron boundaries respectively. These dinucleotides and the often highly conserved surrounding sequences are known as splice sites and serve to bind the protein factors required to perform the cleavage and ligation reactions.

The consequences for mutation occurring within a splice site may, be a reduction in the amount of mature mRNA produced and/or utilization of alternative but incorrect splice sites in the vicinity. The result is production of mRNA which either contains additional intron sequence or which may lack a portion of coding sequence. Where mutation occurs within the 5' (donor), splice site and prevents binding of protein factors, the exon is no longer recognised as such and is excised along with its neighbouring introns. This is referred to as 'exon skipping' (as reviewed by Cooper and Krawczak, 1994 Human Gene Mutation. Bios Scientific Publishers, Oxford, UK, 1994).

In the mutation identified here the G of the conserved GT pair at the exon17/intron17 boundary region is altered to an A. That there is an alteration in the messenger RNA that is translated into protein and that the presence of the change correlates with the white/patched phenotypes suggests that this is the functional mutation rather than merely a linked marker. The splice variant is expected to give rise to a defective protein as 41 amino acids in the mature protein are missing. We therefore assume that this splice mutation is the causal mutation for the difference between I and I$^P$. Our current knowledge as regards molecular differences between alleles at the I locus is summarised in Table 1. In conclusion, we have identified two functionally important mutations. One is the gene duplication present in I$^P$, I* and I which by itself appears to cause the patch phenotype. The exact reason for this phenotypic effect is not known but one can speculate on the basis of comparative data from the mouse that the duplicated copy of the KIT gene may lead to a defect in gene expression which in turn affects melanocyte migration. This is especially valuable in that there can be no breakdown of the linkage between the DNA polymorphism and the trait itself. This has allowed us to develop a range of assays for the determination of the presence of the DNA polymorphism and the genotype of the animal with regard to coat colour determination to a significantly greater extent than has been possible before. The second mutation is the splice mutation that occurs in one of the KIT copies associated with the dominant white (I and I*) alleles. The expression of a truncated form of the KIT protein is expected to cause a more severe defect in KIT function and a more severe effect on coat colour.

TABLE 1

| Allele | KIT gene | Intron 17 | Associated Phenotype |
|---|---|---|---|
| i | KIT1 | Normal | Coloured |
| I$^P$ | KIT1 | Normal | Patch |
|  | KIT2 | Normal |  |
| I | KIT1 | Normal | Dominant White |
|  | KIT2 | Mutated |  |
| I* | KIT1 | Normal | Dominant White |
|  | KIT2 | Mutated |  |

In addition to these two functionally important mutations, a mutation in the KIT gene with no known phenotypic effect, the 4 bp deletion in intron 18 has been documented at the I locus as described in International patent application No. PCT/GB96/01794.

Thus, in a first aspect the present invention provides a method for determining coat colour genotype in a pig which comprises:
(a) obtaining a sample of pig nucleic acid; and
(b) analysing the nucleic acid obtained in (a) to determine whether a mutation is/is not present at one or more exon/intron splice sites of the KIT gene.

In particular, the method determines whether a mutation is/is not present at the exon 17/intron 17 boundary, eg the substitution of the G of the conserved GT pair for A.

Reverse Transcriptase based Polymerase Chain analysis (RT-PCR) of the exon 16-19 region of KIT mRNA in animals of the Large White breed (I/I) and comparison to that transcribed in Hampshire animals (i/i) revealed an extra species of molecule in the former animals. RT-PCR analysis of both breeds yielded a product fragment with a length of 424 bp indicating that both types of animal contained a KIT mRNA transcript containing a region corresponding to this region of the gene. However in addition the I/I animals yielded a RT-PCR product of 301 bp indicating the presence of an mRNA species which did not contain the full transcription of the exon 16-19 DNA sequence (see example 1).

These two transcripts have been shown to be derived from the separate duplicate copies of the KIT gene associated with the I allele. Sequencing over the KIT exon 17/intron 17 boundary revealed a difference in the intron boundary sequences present in the two duplicate copies of the KIT gene associated with the I allele (see example 2). The sequences are as shown below:

| Allele | Kit Gene | Exon 17 | Intron 17 |
|---|---|---|---|
| i | KIT1 | .....AAC | GTG..... |
| I$^P$ | KIT1 | .....AAC | GTG..... |
| I$^P$ | KIT2 | .....AAC | GTG..... |
| I | KIT1 | .....AAC | GTG..... |
| I | KIT2 | .....AAC | ATG..... |

This alteration of the 5' intron splice site from a GT pair to an AT pair affects the splicing of the pre mRNA and results in the loss of the whole of exon 17 from the mRNA transcribed from the I-KIT2 sequence. This will result in a modified KIT protein with the associated alterations in function and phenotype. Based upon the sequence polymorphism rapid tests can be developed to determine the alleles carried by a specific animal at the dominant white locus.

In one form such a test would comprise amplification of the region through the polymerase chain reaction (PCR) utilising genomic DNA from the animal in question as a template. The nucleotide sequence CATG comprises a recognition sequence for the restriction enzyme NlaIII. This sequence is only present in the I-KIT 2 sequence at the junction position and thus one can differentiate the DNA molecules amplified from the two alleles by digestion of the amplification products with this enzyme or any other restriction enzyme with a suitable recognition site.

Genomic DNA for use in such a test can be prepared by a wide range of available methods, from any tissues or products derived from the animal in question. A 175 bp fragment of the KIT gene containing the exon 17/intron 17 boundary region can be amplified from porcine genomic DNA using a pair of primers such as:

KIT21 (5'-GTA TTC ACA GAG ACT TGG CGG C-3') (SEQ. ID No. 1); and

KIT35 (5'-AAA CCT GCA AGG AAA ATC CTT CAC GG-3') (SEQ. ID No. 2).

The use of such primers in a PCR-RFLP test yields a fragment of 175 bp before digestion with NlaIII. In alleles with the G present at nucleotide position 1 of intron 17 (I-KIT1 type sequence) there is only one NlaIII cleavage site present 41 bp from the end of the fragment. This site is present in all versions of the KIT sequence. Thus digestion of the 175 bp fragments obtained from i and I$^P$ alleles yields two fragments of 134 bp and 41 bp. Where the G is miutated to A as in the I-KIT2 sequence present in I and I* a further NlaIII cleavage site is created and thus digestion yields products of 80 bp and 54 bp and 41 bp (see FIG. 3, example 2). A number of other oligonucleotides suitable as PCR primers could easily be derived from the sequence of this region of the porcine genome. An example of such a PCR-RFLP test is given in example 3. The results that would be obtained from such a PCR-RFLP test described above are as shown below:

| Genotype | Fragment sizes 134 + 41 bp | Fragment sizes 80 + 54 + 41 bp |
|---|---|---|
| I/I | Yes | Yes |
| I/I$^P$ | Yes | Yes |
| I/i | Yes | Yes |
| I$^P$/I$^P$ | Yes | No |
| I$^P$/i | Yes | No |
| i/i | Yes | No |
| I*/I | Yes | Yes |
| I*/I* | Yes | Yes |
| i/I* | Yes | Yes |
| I*/I$^P$ | Yes | Yes |

Thus, simply by analysing restriction products certain genotypes cue be distinguished. However, there are others which cannot be distinguished in this first configuration of the test. In a further refinement the test can be carried out in such a way that the amount of each fragment can be calculated. By carrying out electrophoresis on an apparatus that allows the quantification of each of the bands one can determine the ratio of the two forms of template in the genoric DNA sample used. Examples of such an apparatus include the Perkin Elmer Applied Diosystems 373 and 377 DNA sequencing systems. The application of this type of equipment is illustrated in example 4. Any equipment capable of determining the relative amounts of the products from the two different sequences is equally applicable to such tests. The expected results from such a test are shown below.

| Genotype | Normal KIT sequence Copies | Splice mutant KIT Copies | Ratio Normal Splice mutant |
|---|---|---|---|
| I/I | 2 | 2 | 1 |
| I/I$^P$ | 3 | 1 | 3 |
| I/I* | 2 | 2 | 1 |
| I/i | 2 | 1 | 2 |
| I$^P$/I$^P$ | 4 | 0 | 0 |
| I$^P$/I* | 3 | 1 | 3 |
| I$^P$/i | 3 | 0 | 0 |
| I*/i | 2 | 1 | 2 |
| I*/I* | 2 | 2 | 1 |
| i/i | 2 | 0 | 0 |

Thus, using such a test one could identify all animals carrying alleles of dominant white that might dispose themselves or their offspring to exhibiting non-white coat colour (i or I$^P$) as those giving a ratio other than one. Depending on the requirement and the derivation of the lines under selection one could take an appropriate subset of animals. For example in a cross derived animals carrying only alleles I and i one could identify any white individuals (I/I or i/i) carrying i as they would have a ratio in the test of 2 as opposed to I for the I/I animals. The distinction of alleles I and I* can be carried out on the basis of the 4 bp deletion as described in the previously filed patent publication WO97/05278.

There are a range of techniques by which differentiation of alleles containing the splice mutation and those containing the normal sequence could be differentiated by a person expert in the field.

Analysis of the genetic composition of an animal could be based upon a number of different source materials. These include genomic DNA, RNA and the KIT protein itself. There may also be effects on the levels and nature of other proteins, metabolites and RNA species which could be measured to create a more indirect assay.

DNA could be used as the basis for a number of approaches to test one approach is through the amplification of the region of DNA containing the polymorphism using the polymerase chain reaction. This could then be liaised to a number of forms of analysis of the product. Examples of electrophoresis based technologies include Single Strand Conformation Polymorphism (SSCP), Restriction Fragment Length Polymorphism (RFLP) and DNA sequencing of PCR products or direct genome sequencing. Other PCR based techniques that might alternatively be used include the Perkin Elmer TaqMan systems, Single Nucleotide Polymorphic Extension (SNuPE) and Minisequencing. PCR products from the region might also have application in hybridization based approaches to the differentiation of alleles at this locus. Hybridization methods might include the probing of Southern transfers of genomic DNA with allele specific oligonucleotide, RNA, DNA fragment or Protein Nucleic Acid (PNA) probes. Other strategies of application here include hybridization of genomic DNA or PCR products (specific or whole genome) to oligonucleotide arrays possibly in the form of 'DNA chips'. Such arrays could consist of any reagent capable of binding DNA or RNA derived from the locus in question in an allele specific manner. Further useful methods of analysis also include oligonucleotide ligation assay and the ligase chain reaction. For a review on methods for detecting point mutations see Landegren, 1996, Laboratory Protocols for Mutation detection, Oxford University press, Oxford.

A number of effects on the RNA produced from the gene in question have already and may in the future be observed. All such differences between the mutated and normal forms of the gene are useful targets for the determination of genotype and a large range of methods are available to the person skilled in the art. The changes that are or might be observed and methods of analysis are as follows. Alteration of the size rate of processing, stability and quantity of RNA transcripts could be measured through widely used techniques such as northern blotting and RT-PCR as well as a number of the techniques described above for DNA analysis such as hybridization to oligonucleotide or DNA fragment arrays.

Another approach which can be used is to use a linked genetic polymorphism which is closely associated with the presence or absence of the alteration at the exon/intron boundary. Such a polymorphism may occur in the KIT gene itself or in a chromosomal region linked to KIT. By using a single linked marker in complete association with the presence absence of the duplication or a combination of markers showing a partial association a highly informative test can be developed. For instance, the SSCP (Single Strand Conformation Polymorphism) method may be used to develop such polymorphism. The principle of the method is that double-stranded DNA, produced by PCR, is denatured into single-stranded DNA which is then separated by non-denaturing gel electrophoresis. Under non-denaturating conditions the single-stranded DNA forms a secondary structure due to intra-strand interaction but a proportion of the single-stranded DNA will renature and form double-stranded DNA. Two types of polymorphism may be revealed by this method. Firstly, a difference in nucleotide sequence between two alleles may influence the secondary structure of single-stranded DNA which is revealed as a difference in the mobility rate during electrophoresis. Secondly, a difference in nucleotide sequence often influences the mobility of the heteroduplex DNA (A heteroduplex is a double-stranded DNA molecule formed by two single-stranded molecules representing different alleles).

Association between genetic markers and genes responsible for a particular trait can be disrupted, by genetic recombination. Thus, the closer the physical distance between the marker and the gene in question, the less likely it is that recombination will separate them.

It is also possible to establish linkage between specific alleles of alternative DNA markers and alleles of DNA markers known to be associated with a particular gene (e.g. the KIT gene discussed herein), which have previously been shown to be associated with a particular trait. Thus, in the present situation, taking the KIT gene, it would be possible, at least in the short term, to select for pigs with a particular coat colour, indirectly, by selecting for certain alleles of a KIT gene associated marker through the selection of specific alleles of alternative chromosome 8 markers. Examples of such markers known to be linked to the KIT gene on porcine chromosome 8 include genetic polymorphism in the KIT gene itself or in the closely linked genes for the α-subunit of platelet derived growth factor (PDGFRA) and albumin.

Particular genetic markers associated with the KIT gene are microsatellites. These are simple sequence repeats of 4, 3 or, more usually, 2 nucleotides, which occur essentially at random around the genome at approximately every 50,000 bases (about 60,000 microsatellites per haploid genome). Stuttering of DNA polymerase during replication and unequal crossing-over during recombination are thought to result in the loss or gain of repeat units. This means that microsatellites are usually polymorphic and can have several repeat length alleles.

Examples of linked microsatellite sequences include S0086 (Ellegren et al, *Genomics*, 16:431–439 (1993)), S0017 (Coppieters et al, *Animal Genetics* 24:163–170 (1993)), Sw527, Swr750 and SW916 (Rhorer et al, *Genetics*, 136:231–245 (1994)). It would be possible to select indirectly for alleles of the KIT gene linked to coat colour using any of the above markers, or indeed any other linked markers on porcine chromosome 8.

Alterations in the level of the KIT protein could be measured using either specific antibodies for example in an ELISA system or on western blots or through the use of a range of biochemical techniques to measure the activity of the protein. Such tests could also be applied to other proteins or metabolites, the level or nature of which is altered by the presence of specific alleles at the locus. Different protein structures due to the presence of specific alleles could be identified through the use of structure specific antibodies. As with the DNA and RNA based methods all these protein methods could be applied in a quantitative fashion thus achieving the full discriminatory capabilities possible.

Kits could be produced for the specific analysis of the polymorphism described here alone and also with reagents allowing the combined analysis of the other polymorphisms previously reported and the subject of patent publication WO97/05278.

Figure 2:
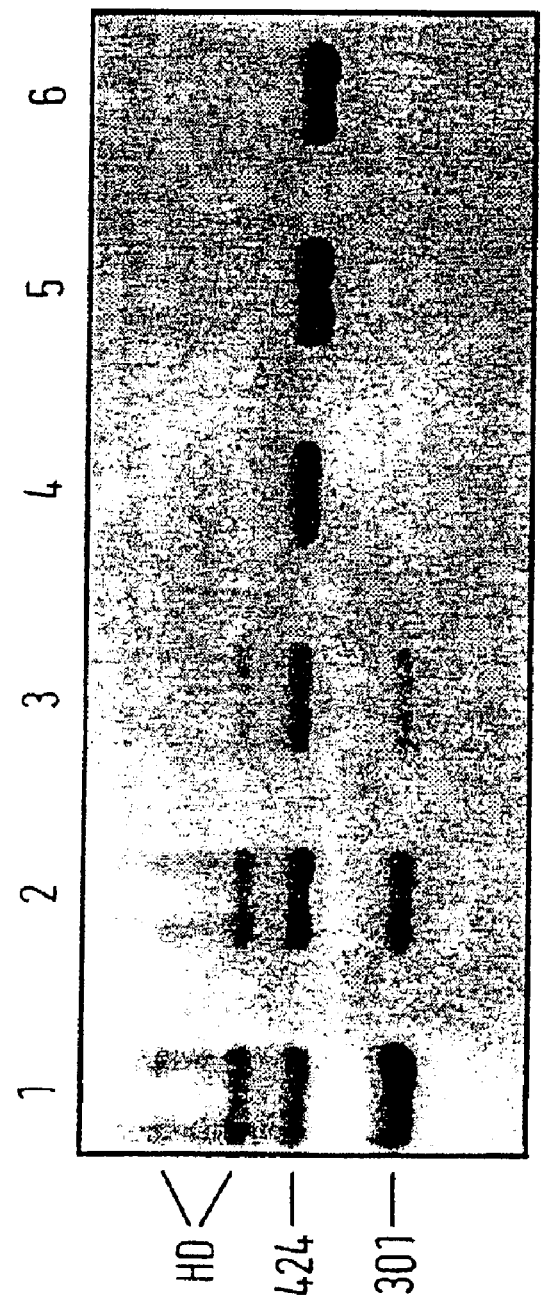
Figure 4C:
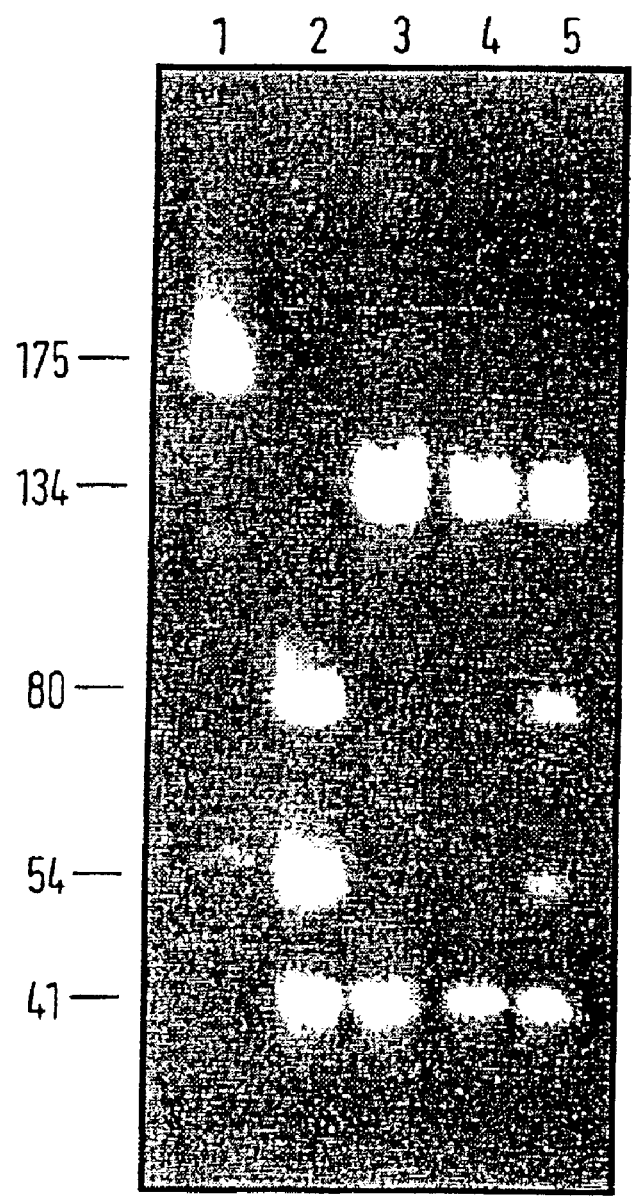
Figure 5:
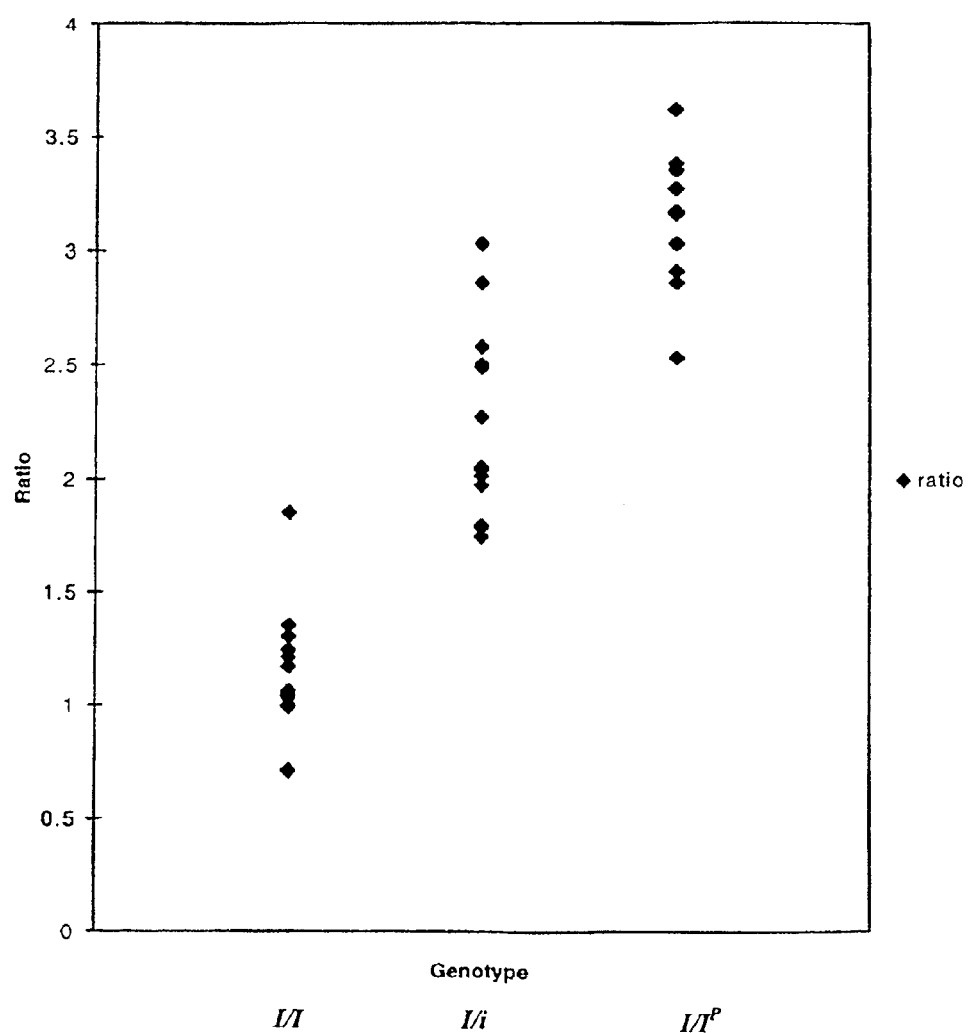

The invention will now be described with reference to the following examples, which should not be construed as in any way limiting the invention. The examples refer to the figures in which:

FIG. 1: is a schematic representation of the structure of the known porcine KIT alleles, where 4 bp del'n refers to the 4 bp deletion in intron 18 of one copy of the duplicated KIT gene DNA as reported by Moller et al. 1996 and Exon 17-A refers to the change of nucleotide 1 of intron 17 from a G as in the wild type allele to an A as reported in this patent;

FIG. 2: shows an electropherogram (4% agarose Nusieve/ Seakem 3:1; 100V for 80 min) showing RT-PCR products of KIT exon 16-19 with the primers KIT1F and KIT7R. The samples 1-3 and 4-6 are Swedish, Large White and Hampshire pigs, respectively. The size difference between the 424 and 301 bp fragments is due to lack of exon 17 in the latter fraction. The two upper bands of the Yorkshire pigs were interpreted as heteroduplexes (HD);

FIG. 3 shows a 48 bp sequence comprising 21 bp of KIT exon 17 and 27 bp of KIT intron 17 where the position of the intron/exon border is marked with a vertical line, the splice site mutation (nt1$^{G \rightarrow A}$) indicated with a vertical arrow and identical bases in allele I$^P$ and i are marked with a dot. The KIT1 gene is included in the sequence listing as SEQ ID NO:10, while the KIT2 gene of allele I is included in the sequence listing as SEQ. ID NO:11;

FIG. 4: shows the results of NlaIII PCR RFLP test used to detect the presence of a splice site mutation in intron 17 of the KIT gene. FIG. 4A shows the position of two NlaIII recognition sites within the PCR product amplified using primer pair KIT21 and KIT35. All distances are given in base pairs. FIG. 4B shows the size of fragments which result following NlaIII digestion of either normal KIT or splice mutant KIT. FIG. 4C illustrates use of the PCR RFLP test. Lane 1 shows the KIT1/KIT35 amplified fragment undigested. Digestion was performed on PCR products amplified from, in Lane 2: a clone which contains the splice site mutation; Lane 3: a clone which contains the normal splice site sequence; Lane 4: genomic DNA from a coloured pig; Lane 5: genomic DNA from a white pig. Fragment sizes are given in base pairs;

FIG. 5: shows a comparison of the ratio of normal to splice mutant KIT in animals of genotypes I/I, I/i and I/I$^P$.

Figure 6:
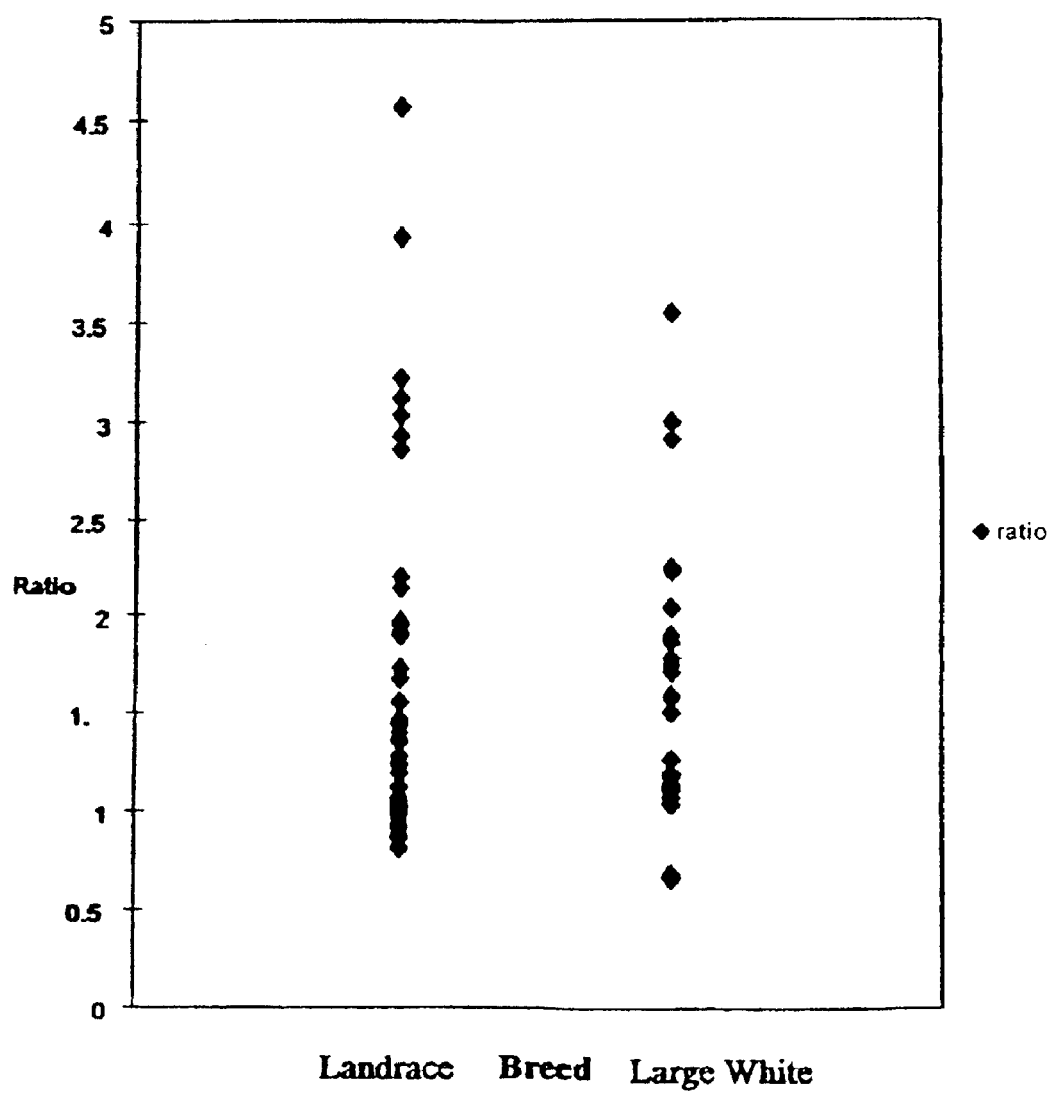
Figure 7:
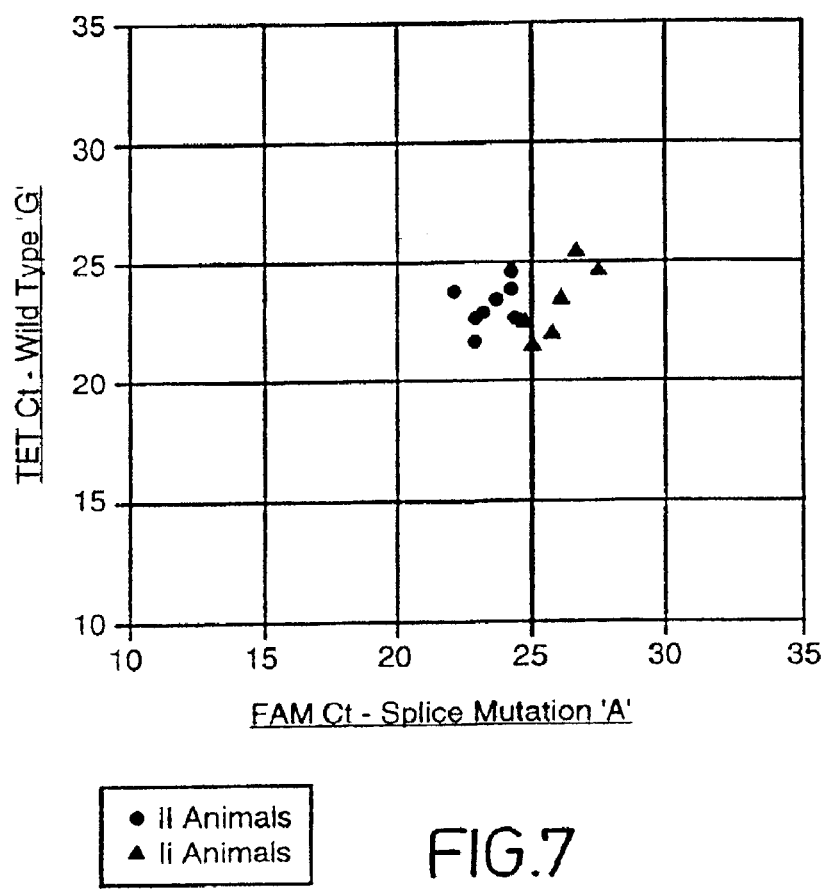

FIG. 6: shows the ratio values for 56 Landrace and 33 Large White animals. A clearly bimodal distribution is observed with 7 Landrace and 3 Large White individuals having a ratio value of approximately 3 or above, suggesting them to be heterozygous carriers for the I$^P$ allele (genotype I/I$^P$). This means I$^P$ has gene frequency estimates of 6.25% (7/112 chromosomes tested) and 4.5% (3/66 chromosomes tested within the Landrace and Large White breeds respectively; and FIG. 7: shows a plot of Ct FAM versus Ct TET for animals of genotypes Ii and II analysed for KIT splice mutant genotype using TaqMan® chemistry.

EXAMPLE 1

RT-PCR of Porcine KIT Exon 16-19 i. mRNA Purification from Blood Samples

Fresh blood samples were collected in citrate tubes from coloured Hampshire pigs and Large White pigs. Leukocytes were isolated from 5 ml blood using Ficoll 100 (Pharmacia Biotech). Isolation of mRNA from leukocytes was then carried out using the Quickprep Micro mRNA purification kit (Pharmacia Biotech). The mRNA was stored as a precipitate under ethanol at −70° C. for up to one month before use in reverse transcriptase (RT)-PCR.

ii. RT-PCR of KIT Exon 16-19

First strand cDNA synthesis was accomplished using the First-Strand cDNA Synthesis kit (Pharmacia Biotech) so that ~100 ng mRNA was randomly primed by 0.1 µg pd(N6) in a total volume of 15 µl. Two µl of the completed first cDNA strand reaction was then directly used per 12 µl PCR reaction by adding 10 µl PCR mix containing 10 pmol each of the mouse/human derived primers KIT1F and KIT7R (5'-TCR TAC ATA GAA AGA GAY GTG ACT C (SEQ. ID No. 3) and 5'-AGC CTT CCT TGA TCA TCT TGT AG (SEQ. ID No. 4), respectively; Moller et al. 1996, supra), 1.2 µl 10×PCR-buffer (10 mM Tris-HCl, pH 8.3, 50 mM KCl) and 0.5 U of AmpliTaq polymerase (Perkin-Elmer) incubated with an equal amount Taqstart antibody (Clonetech) at 25° C. for 5 min to achieve a hot start PCR. The reaction was covered with 20 µl mineral oil and thermocycled in a Hybaid Touchdown machine (Hybaid) with 40 cycles at 94° C. for 1 min, 55–48° C. (touchdown one degree per cycle the first seven cycles and then 48° C. in the remaining cycles) for 1 min and 72° C. for 1 min. After PCR 2 µl loading dye was added to each sample which were then loaded on 4% agarose gel (Nusieve/Seakem 3:1, FMC Bioproducts) and electrophoresed with 100V for 80 min. Products were visualised by ethidium bromide staining and UV-illumination.

iii. Cloning and Sequencing of RT-PCR-products

The-RT-PCR products representing KIT exon 16-19 were purified by extraction from 2% agarose gels using the QIAEX gel extraction kit (QIAGEN and cloned into the pUC18 vector using the Sureclonc ligation kit (Pharmacia Biotech). Plasmids were isolated using the QIAFilter plasmid Midi kit (QIAGEN). Cloned plasmid inserts were sequenced using dye primer chemistry. Each cyclimg reaction was prepared with plasmid template DNA and ready reaction mix containing fluorescently labelled M13 forward or reverse pruiner as described in the ABI Prism protocol P/N 402113 Perkdn Elmer). Cycling and sample pooling were performed using a Catalyst 800 Molecular Biology Workstation (ABI) following the instruments user manual (Document number 903877, Perkin Elmer). The resulting extension products were purified, loaded and analysed using the 377 ABI Prism sequencer as described by the instrument protocol P/N 402078 (Perkin Elmer).

iv. Results and Discussion

A 424 bp fragment including KIT cDNA exon 16-19 was amplified from all pigs. The Hampshire pigs did not show any additional products whereas the Large White pigs (eight tested) all showed a 301 bp truncated cDNA fragment (FIG. 2). Sequence analysis revealed the 424 bp fragment was identical in the two breeds whereas the whole exon 17 (123 bp) was missing from the 301 bp fragment. Apparent differences between individuals regarding the relative amounts of these two products may have been caused either by different genotypes containing differing numbers of copies of the KIT gene sequence, individual differences in mRNA expression levels or random RT-PCR effects.

The two upper fragments present in Large white pigs represent heteroduplexes between the 301 and 424 bp fragments (FIG. 2). This was shown by an experiment where these slow migrating fragments were generated by pooling homoduplexes of the 424 and 301 bp which were then heat denatured and cooled to 25° C. Moreover, cloning of the lower heteroduplex fraction of a Large White pig resulted in clones with insert length corresponding to either of the two hpmoduplexes.

EXAMPLE 2

PCR Amplification and Sequencing of KIT Exon 17-Intron 17 (5' Splice Site)

i. PCR to Produce DNA Sequencing Template

A 175 bp region including the boundary between exon 17 and intron17 of the KIT gene was amplified for sequence analysis using forward primer KIT21 (5'-GTA TTC ACA GAG ACT TGG CGG C-3') (SEQ. ID No. 1); and reverse primer KIT35 (5'-AAA CCT GCA AGG AAA ATC CTT CAC GG-3') (SEQ. ID No. 2). PCR was carried out on a DNA thermal cycler (Perkin Elmer 9600) in a total volume of 20 µl containing 25 ng genomic DNA, 1.0 mM $MgCl_2$, 50 mM KCl, 10 mM Tris-HCl, pH 8.3, 200 µM dNTPs, 0.5 U AmpliTaq Gold (Perkin Elmer) and 10 pmol of both KIT21 and KIT35 primer. To activate AmpliTaq Gold, initial heat denaturation was carried out at 94° C., 45 sec at 55° C. and 45 sec at 72° C. The final extension lasted for 7 min at 72° C. PCR products were cloned into vector pUC 18 using the SureClone ligation kit (Pharmacia Biotech).

ii. Preparation of Plasmid DNA

Plasmid DNA was purified from overnight bacterial culture using the Jetstar plasmid midi kit (Genomed) and the resulting DNA diluted to 150 ng/µl.

iii. Sequencing of Plasmid DNA

DNA was sequenced as in example 1 section iii.

iv. Results

A portion of the DNA sequence from exon 17 and intron 17 of the KIT gene was determined and compared between animals with each of these three alleles. FIG. 3 shows that the I allele carries a splice site mutation at position 11 of intron 17. This G to A base substitution is present in one of the two gene copies carried on each chromosome. The base substitution occurs in the invariant GT dinucleotide which characterises 5' exon/intron boundaries. Analysis of the $I^P$ allele showed the splice site mutation was not present in either the normal (KIT1) or duplicated copy of the gene (KIT2). We have found the splice site mutation is unique to the I alleles, and therefore makes it possible to distinguish the I-KIT2 sequences.

EXAMPLE 3

Testing For the Presence of the Splice Site Mutation with PCR RFLP

To easily test for the presence of the G to A splice site mutation, restriction endonuclease NlaIII (CATG) was used to exploit the point substitution identified at position 1 of intron 17 (FIG. 3). The NlaIII recognition sites in the fragment amplified from KIT and the expected restriction products are illustrated in FIGS. 4A and 4B respectively.

i. DNA Preparation for RFLP Test

DNA can be prepared from any source of tissue containing cell nuclei, for example white blood cells, hair follicles, ear notches and muscle. The procedure here relates to blood cell preparations; other tissues can be processed similarly by directly suspending material in K buffer and then proceeding from the same stage of the blood procedure. The method outlined here produces a cell lysate containing crude DNA which is suitable for PCR amplification. However, any method for preparing purified, or crude, DNA should be equally effective.

Blood was collected in 50 mM EDTA pH 8.0 to prevent coagulation. 50 µl of blood was dispensed into a small microcentrifuge tube (0.5 ml Eppendorf or equivalent). 450 µl of THE buffer was added to lyse the red blood cells (haem groups inhibit PCR) and the mix vortexed for 2 seconds. The intact white and residual red blood cells were then centerfuged for 12 seconds at 13,000 g in a microcentrifuge. The supernatant was removed by gentle aspiration using a low pressure vacuum pump system. A further 450 µl of THE buffer was then added to lyse the remaining red blood cells and the white blood cells collected by centrifugation as before. If any redness remained in the pellet, this process was repeated until the pellet was white. After removal of the last drop of supernatant from the pelleted white blood cells, 100 µl of K buffer containing proteinase K was added and the mixture incubated at 55 degrees C for 2 hours. The mixture was then heated to 95–100 degrees C for 8 minutes and the DNA lysates stored at −20° C. until needed.

| Reagents | |
|---|---|
| T.E. Buffer: | 10 mM TRIS-HCl pH 8.0 |
| | 1 mM EDTA |
| K Buffer: | 50 mM KCl |
| | 10 mM TRIS-HCl pH 8.3 |
| | 2.5 mM MgCl2 |
| | 0.5% Tween 20 | ii. Restriction Enzyme Digestion and Electrophoresis

The PCR amplification product is 175 bp in length. To test for polymorphism at position 1 of intron 17, digestion reactions were set up as below:

3.0 μl PCR amplified DNA 1.0 μl 10×NEBuffer 4

0.1 μl BSA 100 μg/ml 0.1 μl NlaIII 10 μl 5.8 μl dH2O (1 X NEBuffer 4 (New England Biolabs) contains 50 mM potassium acetate, 20 mM Tris acetate, 10 mM magnesium acetate and 1 mM DMT). Following incubation at 37° C. for 90 minutes each 10 μl reaction volume had 2 μl of loading dye added and the mix loaded on a 8% native polyacrylamide gel (Protogel, 37.5:1 acrylamide-bisacrylamide , National Diagnostics, Atlanta) in 0.5×TBE (44.5 mM Tris pH 8.0, 44.5 mM boric acid and 0.5 mM EDTA) and electrophoresed for 3 hours at 200V in a vertical slab unit (SE600 Hoefer Scientific Instruments). Products were visualised by ethidium bromide staining.

iii. Results

A PCR RFLP protocol was designed to test for the presence of the splice site mutation as the substitution occurs within the recognition site for resticton endonuclease NlaIII. FIG. 4B illustrates that presence of the G to A base substitution at position 1 of KIT intron 17 results in restriction at each of two NlaIII recognition sites within the 175 bp DNA fragment. Following electrophoresis, this results in fragments of sizes 80 bp, 54 bp and 41 bp. Where the splice site mutation is absent however, incubation with NlaIII results in digestion only at recognition site 1. Following electrophoresis this results in fragments of 134 bp and 41 bp. The invariant NlaIII recognition site 1 serves as an internal control to ensure complete digestion has taken place. Results of this PCR RFLP analysis are illustrated in FIG. 4C. Analysis was performed on fragments amplified from clones which either carry the splice site mutation (lane 2) or carry the normal splice site sequence (lane 3). Lane 4 shows the result of analysis where DNA amplified from the genomic DNA of a coloured animal was used. Lane 5 shows the resulting bands where a white animal was tested. The test was used to analyse 121 individuals from seven different breeds of pig. The splice site mutation was found only in the 97 animals with the dominant white phenotype (I/- or I*/i) and none of the 24 coloured ($I^P$ or i) examples (Table 2). This analysis confirms I and I* to be unique in that they are the only alleles to carry the splice site mutation.

TABLE 2

Distribution of the Splice Site Mutation Between Different Breeds and Coat Phenotype

| Breed | Coat Colour | Assumed Genotype[1] | Animals Tested | Normally spliced KIT[2] | Splice Mutation[2] |
|---|---|---|---|---|---|
| Large White | White | I/— | 33 | 33 | 33 |
| Landrace | White | I/— | 56 | 56 | 56 |
| Hampshire | Coloured | i/i | 5 | 5 | 0 |
| Duroc | Coloured | i/i | 5 | 5 | 0 |
| Pietrain | Coloured | i/i | 8 | 8 | 0 |
| Meishan | Coloured | i/i | 5 | 5 | 0 |
| Wild Boar | Coloured | i/i | 1 | 1 | 0 |
| Wild Boar x Large White | White | I*/— | 8 | 8 | 8 |
| Totals | | | | | |
| | White | I/— | 89 | 89 | 89 |
| | White | I*/— | 8 | 8 | 8 |
| | Coloured | i/i | 24 | 24 | 0 |

[1]White animals may be homozygous or heterozygous for the I allele
[2]Presence of the splice site mutation determined by NlaIII PCR RFLP test

EXAMPLE 4

Quantification of Normal KIT and Splice Mutant KIT (Intron 17 $nt1^{G \rightarrow A}$)

As the splice site mutation is present in only one of the duplicated regions of I and not in the duplicated region of $I^P$, the various genotypes can be expected to have the attributes described in Table 3.

TABLE 3

| Genotype | Copies of Normal KIT | Copies of KIT containing the splice mutation | Ratio of normal KIT to splice mutant KIT |
|---|---|---|---|
| I/I | 2 | 2 | 1:1 |
| I/i | 2 | 1 | 2:1 |
| i/i | 2 | 0 | 2:0 |
| I/$I^P$ | 3 | 1 | 3:1 |
| $I^P$/i | 3 | 0 | 3:0 |

Due to the dominance of allele I, three of the genotypes in Table 2 are carried by white animals and therefore can not be identified by phenotypic characterisation. Quantification of the relative amounts of the normal KIT gene and the splice mutant KIT gene allows the ratio between the two to be calculated, and therefore the genotype of individual animals predicted. This was achieved by quantification of two DNA fragments following NlaIII digestion. The amount of 134 bp fragment, representative of the normally spliced KIT gene, and of 54 bp fragment, representative of the splice mutant KIT, were measured following electrophoresis using GeneScan software.

i. PCR to Produce DNA for Quantification

As described in example 2 section i. The reverse primer KIT35 is labelled with the ABI fluorescent dye FAM at the 5' end.

ii. Restriction Enzyme Digestion

As described in example 2 section ii.

iii. Electrophoresis and Quantification of DNA Fragments

Following digestion, 0.5 μl of the reaction volume was mixed with 2.5 μl of deionised formamide, 0.5 μl of GS350 DNA standard (ABI) and 0.4 μl blue dextran solution before being heated to 90° C. for 2 minutes and rapidly cooled on ice. Three μl of this mix was then loaded onto a 377 ABI Prism sequencer and the DNA fragments separated on a 6% polyacrylamide gel in 1×TBE buffer for 2 hours at 700 V, 40 mA, 32 W. The peak area of fragments representative to both the normal and splice mutant forms of KIT were quantitated using the GeneScan (ABI) software.

iv. Ratio Calculations

The peak area value of the 134 bp fragment (normal KIT) was divided by twice the peak area value of the 54 bp fragment (splice mutant KIT) in order to calculate the ratio value for each sample.

v. Results

Analysis was performed on animals from the Swedish wild pig/Large White intercross pedigree for which genotypes at I have been determined by conventional breeding experiments with linked markers. FIG. 5 and Table 4 show the ratio of normal to mutant KIT calculated for animals from each of the three genotype classes, I/I (expected ratio 1:1), I/i (expected ratio 2:1) and I/I$^P$ (expected ratio 3:1). The results are entirely consistent with the expected ratio values and indicate that the three genotype classes can be distinguished using this method.

TABLE 4

Ratio of the Two KIT Forms in Different Dominant White Genotypes in a Wild Pig/Large White Intercross

| Genotype | Phenotype | Expected Ratio (Normal: Mutant) | Observed Ratio (Normal:Mutant) ± SE | Number Tested |
|---|---|---|---|---|
| I/I | White | 1:1 | 1.15 ± 0.075 | 13 |
| I/I$^P$ | White | 3:1 | 3.11 ± 0.084 | 12 |
| I/i | White | 2:1 | 2.23 ± 0.109 | 14 |

FIG. 5 illustrates that the range of ratio values calculated for the two genotypes I/I and I/I$^P$ do not overlap. This enables animals carrying the I$^P$ allele to be identified and the frequency of the allele within different pig breeds determined. Ratio values were calculated for 56 Landrace and 33 Large White animals and the results are shown in FIG. 6. A clearly bimodal distribution is observed with 7 Landrace and 3 Large White individuals having a ratio value of approximately 3 or above, suggesting them to be heterozygous carriers for the I$^P$ allele (genotype I/I$^P$). This means I$^P$ has gene frequency estimates of 6.25% (7/112 chromosomes tested) and 4.5% (3/66 chromosomes tested) within the Landrace and Large White breeds respectively.

EXAMPLE 5

Analysis for Presence and Quantification of the Porcine KIT Splice Mutation using the PE ABI TaqMan Chemistry Method i. Preparation of Template DNA for PCR DNA was prepared as in example 3, section i ii. TaqMan® PCR Reactions TaqMan® PCR reactions were set up as shown in table 5

TABLE 5

PCR mix for TaqMan ® based splice mutation test

| Reagent | Final Conc$^n$ | Volume |
|---|---|---|
| 10x TaqMan ® Buffer A (Perkin Elmer) | 1 x | 2.50 µl |
| 25 mM MgCl$^2$ Sol$^n$ | 5 mM | 5.00 µl |
| DATP | 200 µM | 0.50 µl |
| DCTP | 200 µM | 0.50 µl |
| DGTP | 200 µM | 0.50 µl |
| DUTP | 200 µM | 0.50 µl |
| Amplitaq Gold ™ (5 U/µl) (Perkin Elmer) | 0.05 U/µl | 0.25 µl |
| AmpErase ™ N-Glycosylase (1 U/µl) (Perkin Elmer) | 0.01 U/µl | 0.25 µl |
| KITTM-NEST-F (5 µM) | 500 nM | 2.50 µl |
| KITTM-NEST-R (5 µM) | 500 nM | 2.50 µl |
| KITTM FAM (5 µM) | 100 nM | 0.50 µl |
| KITTM TET (5 µM) | 100 nM | 0.50 µl |
| 25% Glycerol | 8% | 8.00 µl |
| Porcine genomic DNA |  | 1.00 µl |
|  |  | 25.00 µl |

The PCR primers used were as described below:

KITTM-Nest-F (5'-CTC CTT ACT CAT GGT CGA ATC ACA-3') (SEQ. ID No. 6) and

KITTM-Nest-R (5'-CGG CTA AAA TGC ATG GTA TGG-3') (SEQ. ID No. 7).

The TaqMan® probes used were:

KITTM-A-FAM (5'-TCA AAG GAA ACA TGA GTA CCC ACG CTC-3')(SEQ. ID No. 8) and

KITTM-G TET (5'-TCA AAG GAA ACG TGA GTA CCC ACG C-3') (SEQ. ID No. 9)

The TaqMan® probes were prepared by Perkin Elmer and labelled with FAM and TET as indicated as well as the standard quenching group TAMRA. The 10×TaqMan® Buffer A, Amplitaq Gold™, AmpErase N-Glycosylase, NTP's and 25 mM MgCl$_2$ used were part of the TaqMan® PCR Core reagent Kit, supplied by Perkin-Elmer.

The reactions were then placed into a Perkin Elmer ABI Prism 7700 Sequence Detector and the reaction carried out using the following thermal profile, 50° C. for 2 minutes, 95° C. for 10 minutes followed by 40 cycles of 95° C. 15s, 62° C. 60s. The reactions were carried out under the control of 'Sequence Detector V.1.6' software using the 'Single Reporter' and 'Real-Time' options with the 'Spectral Compensation' function activated. Upon completion of the run real-time profiles for each sample were examined on the ABI7700 to check for any samples giving highly irregular profiles which were then excluded. The thresholds for both dyes, Fam and Tet, were set so that they intercepted each dye during the exponential phase of PCR. Following updating of the calculations in 'Sequence Detector V.1.6' software results were exportated into MS Excel for further analysis.

iii. Analysis of Results

Based upon the underlying theoretical principle that one cycle of PCR gives a doubling in the amount of cleavage of the quenching dye from the allele specific probe and therefore doubles the signal one would expect the threshold cycle numbers from the II and Ii genotypes analysed to be as below:

TABLE 6

Theoretical results for TaqMan ® analysis of genotype at the KIT splice mutation

| Genotype | Copies KIT 1 (G) | Copies KIT 2 (A) | Theoretical Ct TET (G) | Theoretical Ct FAM (A) |
|---|---|---|---|---|
| II | 2 | 2 | X | Y |
| Ii | 2 | 1 | X | Y + 1 |

In theory the Ct for TET and FAM signals, represented as X and Y should be the same, as equal numbers of copies of the target sequences should be present in an II animal. However in practice this does not necessarily occurs due to differences in the hybridization and cleavage efficiency of the two probes and variation in the setting of the threshold cycle between the two dye signals. The reduction in splice mutant containing (A) sequences relative to those not containing the splice mutation (G) in the Ii animals ie 2:1 G:A ratio rather than 1:1 as for II genotype, should lead to the FAM signal reaching the theshold 1 cycle later than the TET signal in the genotype Ii animals. The actual resuls for samples tested are shown in Table 7.

TABLE 7

Ct values from analysis of II and Ii genotypes

| Sample | Genotype | Ct FAM (A) | Ct TET (G) | Ct FAM-Ct TET |
|---|---|---|---|---|
| 1 | Ii | 24.68 | 22.59 | 2.09 |
| 2 | Ii | 25.98 | 23.62 | 2.36 |
| 3 | Ii | 26.54 | 25.57 | 0.97 |
| 4 | Ii | 27.37 | 24.78 | 2.59 |
| 5 | Ii | 24.94 | 21.61 | 3.33 |
| 6 | Ii | 25.68 | 22.1 | 3.58 |
| | | | | Ii Mean = 2.49 |
| 7 | II | 22.05 | 23.78 | −1.73 |
| 8 | II | 24.22 | 24.59 | −0.37 |
| 9 | II | 24.19 | 23.85 | 0.34 |
| 10 | II | 23.66 | 23.51 | 0.15 |
| 11 | II | 24.35 | 22.71 | 1.64 |
| 12 | II | 22.82 | 21.69 | 1.13 |
| 13 | II | 22.84 | 22.7 | 0.14 |
| 14 | II | 23.17 | 22.9 | 0.27 |
| | | | | Mean = 0.20 |
| No Template | | 35 | 35 | 0 |
| No Template | | 35 | 35 | 0 |
| No Template | | 35 | 35 | 0 |
| No Template | | 35 | 35 | 0 |

Despite variation around the mean values it can be seen from Table 7 that there is a significantly increased delay in the FAM signal reaching the threshold level (approximately 2 cycles) relative to the TET signal in Ii animals compared to II animals as predicted, reflecting the reduced number of copies of the splice mutant (A) sequence present in animals of the Ii genotype. Plotting of the individual samples on a scatter plot (FIG. 7) shows clustering of the two genotypes with the Ii cluster shifted along the Ct FAM axis due to the reduced number of copies of the KIT2 (A) sequence for which the FAM probe is specific.

---

What is claimed is:

1. A method for determining coat colour genotype in a pig which comprises:
   (a) obtaining a sample of pig nucleic acid; and
   (b) analysing the nucleic acid obtained in (a) to determine whether a mutation is/is not present at an exon 17/intron 17 splice site of a KIT gene, wherein the mutation consists of the substitution of the G in the conserved GT pair by A.

2. The method according to claim 1, wherein the sample of nucleic acid is amplified prior to analysis.

3. The method according to claim 2, wherein the nucleic acid is genomic DNA.

4. The method according to claim 3, wherein amplification is carried out using PCR and at least one pair of suitable primers.

5. The method according to claim 4, wherein the pair of suitable primers is:

5'-GTA TTC ACA GAG ACT TGG CGG C-3' (SEQ. ID No. 1); and

5'-AAA CCT GCA AGG AAA ATC CTT CAC GG-3' (SEQ. ID No. 2).

6. The method according to claim 3, wherein after amplification the nucleic acid is treated with a restriction enzyme, followed by analysis of fragment lengths.

7. The method according to claim 6, wherein the nucleic acid is treated with the restriction enzyme NlaIII.

8. The method according to claim 6, wherein the ratio of restriction fragment lengths is determined.

9. The method according to claim 2, wherein the nucleic acid is mRNA.

10. The method according to claim 9, wherein the nucleic acid is amplified using RT-PCR.

11. The method according to claim 10, wherein the length of RT-PCR product is determined.

12. A method for determining coat colour genotype in a pig which comprises the step of analysing a sample of pig KIT protein to determine whether the protein is a splice variant protein produced by the substitution of G in the conserved GT pair by A, at an exon 17/intron 17 splice site of a KIT gene, said splice variant protein being correlated with coat colour genotype.

13. A kit for use in determining the coat colour genotype of a pig which comprises one or more reagents for carrying out PCR and the following pair of primers:

5'-GTA TTC ACA GAG ACT TGG CGG C-3' (SEQ ID No. 1);

5'-AAA CCT GCA AGG AAA ATC CTT CAC GG-3' (SEQ ID No. 2).

14. The method of claim 1, wherein the presence or absence of said mutation is determined in each copy of the KIT gene in the pig's genome, and the ratio of the number of KIT genes lacking the mutation to the number of KIT genes containing the mutation is determined.

15. The method according to claim 7, wherein the ratio of restriction fragment lengths is determined.

* * * * *